United States Patent

Bohlmann et al.

[11] Patent Number: 6,136,800
[45] Date of Patent: *Oct. 24, 2000

[54] 17-DIFLUOROMETHYLENE-ESTRATRIENES

[75] Inventors: Rolf Bohlmann, Berlin, Germany; Gabor Rubayi, Alamo, Calif.

[73] Assignee: Schering Aktiengesellschaft, Germany

[*] Notice: This patent is subject to a terminal disclaimer.

[21] Appl. No.: 09/263,062

[22] Filed: Mar. 8, 1999

Related U.S. Application Data

[63] Continuation of application No. 08/913,325, Feb. 23, 1998, Pat. No. 6,018,062.

[30] Foreign Application Priority Data

Mar. 13, 1995 [DE] Germany ............... 195 09 729

[51] Int. Cl.⁷ .................................................. A61K 31/56
[52] U.S. Cl. .................. 514/182; 514/824; 514/825; 514/826; 514/866; 514/886; 514/899; 552/530; 552/533
[58] Field of Search ................. 514/182, 824, 514/825, 826, 866, 886; 552/530, 533

[56] References Cited

U.S. PATENT DOCUMENTS

| | | | |
|---|---|---|---|
| 5,124,321 | 6/1992 | Jungblut et al. | 514/182 |
| 5,773,432 | 6/1998 | Kauser et al. | 514/182 |
| 5,783,571 | 7/1998 | Berliner et al. | |
| 5,883,087 | 3/1999 | Berliner et al. | |
| 5,965,552 | 10/1999 | Berliner et al. | |
| 5,969,168 | 10/1999 | Berliner et al. | |

*Primary Examiner*—Barbara Badio
*Attorney, Agent, or Firm*—Millen, White, Zelano & Branigan, P.C.

[57] ABSTRACT

This invention describes the new 17-difluoromethylene-estratrienes of general formula I

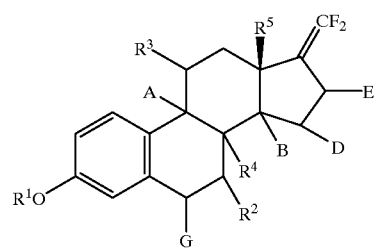

in which $R^1$ is a hydrogen atom or a $C_1$–$C_{10}$ alkyl group, $R^5$ is a methyl or ethyl group, and $R^2$ is a hydrogen atom or a $C_1$–$C_{10}$ alkyl group in α- or β-position, $R^3$ is a hydrogen atom or a $C_1$–$C_{10}$ alkyloxy group in α- or β-position, $R^4$ is a hydrogen atom in α- or β-position, and A, B, D, E and G each is a hydrogen atom, and optionally at least one of substituent pairs G and $R^2$, $R^2$ and $R^4$, $R^4$ and A, A and $R^3$, B and D, D and E is a double bond.

4 Claims, 1 Drawing Sheet

17-DIFLUOROMETHYLENE-ESTRATRIENES

This is a continuation, of prior application Ser. No. 08/913,325, filed Feb. 23, 1998 now U.S. Pat. No. 6,018,062.

This invention relates to 17-difluoromethylene-estratrienes, process for their production and the use of the latter for the production of pharmaceutical products (pharmaceutical agents).

The 17-difluoromethylene-estratrienes according to this invention are characterized by general formula I:

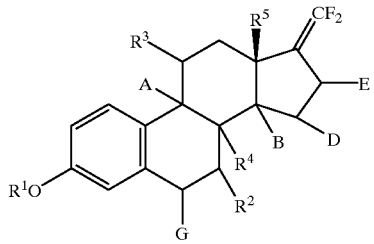

in which
$R^1$ means a hydrogen atom or a $C_1$–$C_{10}$ alkyl group,
$R^5$ means a methyl or ethyl group, and
$R^2$ means a hydrogen atom or a $C_1$–$C_{10}$ alkyl group in α- or β-position,
$R^3$ means a hydrogen atom or a $C_1$–$C_{10}$ alkyloxy group in α- or β-position,
$R^4$ means a hydrogen atom in α- or β-position, and A, B, D, E and G each mean a hydrogen atom, and optionally at least one of substituent pairs
G and $R^2$, $R^4$ and $R^4$, $R^4$ and A, A and $R^3$, B and D, D and E mean a double bond.

The invention preferably relates to those compounds of general formula I, in which
$R^1$ means a hydrogen atom or a $C_1$–$C_{10}$ alkyl group,
$R^5$ means a methyl or ethyl group, and
A, B, D, E, G, $R^2$ and $R^3$ each mean a hydrogen atom and $R^4$ means a hydrogen atom in β- or α-position, or
$R^2$ with $R^4$, $R^4$ with A, A with $R^3$, B with D, D with E or G with $R^2$ mean an additional bond and the others of these substituents each mean a hydrogen atom, or
$R^2$ means a $C_1$–$C_{10}$ alkyl group in β-position, whereby then A, B, D, E, G, $R^3$ and $R^4$ each stand for a hydrogen atom, or
$R^3$ means a $C_1$–$C_{10}$ alkyloxy group in β-position, whereby then A, B, D, E, G and $R^2$ and $R^4$ each stand for a hydrogen atom.

The $C_1$–$C_{10}$ alkyl or alkoxy groups that occur in radicals $R^1$, $R^2$ and $R^3$ are a methyl, ethyl, n-propyl, isopropyl, n-butyl, isobutyl or tert-butyl radical, or their higher straight-chain or branched-chain homologues or, in the case of $R^3$, a corresponding alkoxy radical. The methyl or methoxy radical is preferred.

A hydrogen atom preferably stands for $R^1$.
Primarily a methyl group is suitable for $R^5$.
In addition, the compounds of general formula I in which A, B, D, E, G, $R^2$, $R^3$ and $R^4$ are hydrogen atoms or in which A, B, D, E, $R^3$ and $R^4$ are hydrogen atoms and G with $R^2$ means an additional bond are preferred.

The compounds mentioned below are especially preferred according to this invention:
17-Difluoromethylene-estra-1,3,5(10)-trien-3-ol
17-difluoromethylene-estra-1,3,5(10),6-tetraen-3-ol
17-difluoromethylene-11β-methoxy-estra-1,3,5(10)-trien-3-ol
17-difluoromethylene-estra-1,3,5(10),7-tetraen-3-ol
17-difluoromethylene-estra-1,3,5(10),8-tetraen-3-ol
17-difluoromethylene-estra-1,3,5(10),9(11)-tetraen-3-ol
17-difluoromethylene-3-methoxy-estra-1,3,5(10),15-tetraene
17-difluoromethylene-estra-1,3,5(10),15-tetraen-3-ol
17-difluoromethylene-7β-methyl-estra-1,3,5(10)-trien-3-ol
17-difluoromethylene-8α-estra-1,3,5(10)-trien-3-ol
17-difluoromethylene-3-methoxy-18-methyl-estra-1,3,5(10)-triene
17-difluoromethylene-18-methyl-estra-1,3,5(10)-trien-3-ol.

The compounds that come closest in structure to these compounds are the 17-monohalomethylene-estratrienes that are described in EP-A 0 320 438.

The known 17-halomethylene-estratrienes show a lesser affinity to the estrogen receptors than estradiol and cause increased cell membrane and blood/lymphatic permeability in comparison with estradiol. These compounds are therefore especially well suited for treating symptoms that occur owing to failure of the second action of estradiol (menopausal symptoms).

The new 17-difluoromethylene-estratrienes according to the invention show new, completely unexpected pharmacological properties not described until now for the above-mentioned 17-monohalomethylene-estratrienes and other steroids.

The 17-difluoromethylene-estratrienes are very weak estrogens, as was possible to show based on standard bonding studies on the estrogen receptor and in transactivation assays, in which 17β-estradiol was used in each case as a comparison substance (M. T. Bocquel et al., Nucleic Acid Research 17:2581–95; S. Green et al., Nucleic Acid Research 16:369, 1989; L. Tora et al., EMBO J. 8:1981–86, 1989; J. E. Burch et al., Mol Cell. Biol. 8:1123–31, 1988).

It has been found that the 17-difluoromethylene-estratrienes exhibit, surprisingly enough, antioxidative and vasculoprotective properties and are therefore suitable for treating and preventing the most varied diseases (e.g., Sieg-fried et al., JPET 260:668, 1992; Chao et al., J. Immunol. 149:2736, 1992; Corbett & McDaniel, Diabetes, 41:897, 1992; Siminiak et al., Intl. J. Cardiol., 45:171, 1994).

To characterize compounds with hypothesized antioxidative and vasculoprotective properties, various test methods are used, whose results overall make it possible to make a statement on whether the tested compounds have antioxidative and vasculoprotective properties.

The antioxidative and vasculoprotective properties of the new compounds are based both on a direct action by prevention of the oxidation of the LDL's and on an indirect action by release of the vasodilator nitrogen oxide (NO) from endothelial cells.

Experimental Methods and Findings
LDL Oxidation

Since oxidative modifications of lipoproteins may play a role in the development of arteriosclerosis (Steinberg et al., N. Engl. J. Med. 320:915, 1989; Esterbauer et al., Free Radical Biology & Medicine 13:341, 1992), the compounds of general formula I were examined with regard to their ability to influence the oxidation of LDL's (low density lipoproteins). To determine the antioxidative abilities of the compounds of general formula I, an assay was developed, which was based on methods of Vedie (J. Lipid. Res. 32:1359–69, 1991).

For this purpose, the alterations of the chromatographic behavior of human LDL owing to copper ions of induced oxidation are measured.

Human LDL was ordered from Organon Teknika, Rockville, Md. It was diluted with Ca and Mg ions in free PBS (phosphate buffer solution) to a protein concentration of 0.5 mg/ml, and dialyzed at 4° C. on this buffer to remove EDTA (ethylenediamine-tetraacetic acid) before oxidation.

LDL was then oxidized by the addition of 10 μmol of copper sulfate and subsequent incubation at 37° C. in a water bath, in an open Eppendorf vessel. The test compound, dissolved in DMSO (dimethyl sulfoxide), was added to it at a final volume of 1%. The oxidation was stopped by the addition of 1 mmol of EDTA. The samples were stored until FPLC (fast protein liquid chromatography) analysis was done at 4° C. It was noted that the chromatographic behavior of the oxidized LDL's remained constant for longer than one week.

FPLC Analysis

The samples (0.1 ml with 0.5 mg of LDL protein) were analyzed on a 1 ml Q-sepharose column (Hi-Trap Q. Pharmacia). The absorption was measured constantly at 280 nm, and the peaks were integrated for a quantification.

The starting buffer (buffer A) consisted of 10 mmol of tris-HCl, pH 7.5 with 1 mmol of EDTA. Under these conditions, LDL bonded completely to the column. It was eluted with a step gradient of buffer B (buffer A+1 M of NaCl).

Five fractions were analyzed (delineated): fraction A (0.2 M of salt), fraction B (0.3 M of salt), fraction C (0.4 M of salt), fraction D (0.5 M of salt) and fraction E (0.6 M of salt). Unmodified commercial LDL behaves somewhat inconsistently. It was completely eluted in fractions A+B. During the incubation time with copper sulfate, LDL was modified more and more, so that it eluted at higher salt concentrations. Within the first hour of incubation, a portion of the protein in fraction C was found by copper. After 3–4 hours, the protein was almost completely eluted in fractions C and D. After 24 hours, all proteins had been converted to one form or forms, which eluted in fractions D+E.

The degree of oxidation of LDL is determined with the aid of the oxidation index.

Oxidation index:(%)=100×Σ (peak range in fractions C-E (0.4–0.6 M)]Σ[peak range in fractions A-E(0.2–0.6 M)]

In a 3- to 4-hour copper-induced oxidation, a range of 60–90% was found for the LDL that was not treated with the substance according to general formula I. Only rarely was a significantly lower oxidation index observed. All experiments in which the oxidation index in the positive control did not reach at least 60% were not taken into consideration. The addition of 1 mmol of EDTA during incubation with copper (negative control) prevented the alterations of LDL chromatography mobility (oxidation index 0%).

The effects of the 17-difluoromethylene-estratrienes on the copper-induced LDL oxidation show (Table 1) that the latter protect the LDL's before an oxidation (whereby estradiol shows an even more antioxidative action than the 17-difluoromethylene-estratrienes).

TABLE 1

Results of the Cu-Induced Oxidation of LDL

| Substances | Oxidation Index |
| --- | --- |
| positive control | 86.7% |
| negative control (EPTA) | 26.1% |
| 17β-E$_2$ | 19.9% |

TABLE 1-continued

Results of the Cu-Induced Oxidation of LDL

| Substances | Oxidation Index |
| --- | --- |
| compound A (17-difluoro-methylene-11β-methoxy-estra-1,3,5(10),6-tetraen-3-ol | 44.8% |

2. Vasorelaxation of Isolated Rat Aortas

The aortas of male Sprague-Daweley rats were removed, freed from all adherent fat and connected tissue and cut into 2 mm rings. The endothelium was mechanically removed from the inner vascular surfaces of several aorta rings. The rings were suspended separately in 10 ml organ baths at 37° C., which contained Krebs-Henseleit solution (KHS), which has a pH of 7.4 if it is saturated with 95% $O_2$ and 5% $CO_2$. Before the beginning of the test, the tissue was allowed to balance at 1 g of vapor pressure for 90 minutes. The isometric vapor pressure was measured with a "force transducer" (Grass FT03C) and recorded on a recorder (Gould TA 5000). All tissues were contracted with KCl (30 mmol) and then washed three times in fresh KHS. The vascular rings were contracted either with 30 mmol of KCl or 100 mmol of phenylephrines (PE). To check the presence or absence of endothelium, 1 μmol of acetylcholine (Ach) was added to the tissue. Concentration-relaxation curves for 17β-estradiol and 17-difluoromethylene-11β-methoxy-estra-1,3,5(10),6-tetraen-3-ol (compound A) were obtained by the cumulative addition of the substances to be tested in semilogarithmic concentration components to the tissue baths. The answers were calculated as percentage changes in contraction and depicted graphically in FIGS. 1 and 2. In this case, E stands for endothelium and + or − means tissue with (+) or without (−) endothelium.

In summary, it can be noted that
the new 17-difluoromethylene-estratrienes in isolated rat aortas produce relaxation of the smooth muscles; in contrast to 17β-estradiol, which exerts its relaxing effect on the aorta, independently of the endothelium, the new compounds induce vasorelaxation by release of NO from the endothelium.

These results of the pharmacological tests show that the new compounds of general formula I exhibit vasculoprotective properties, since
vascular relaxation protects the vessels from the consequences of increasing local (vasospasms in the coronary and cerebral arteries) or general (e.g., hypertension) muscle tone of the smooth muscles;
the release of NO from the endotheliurm results in vasorelaxation (Furchgott & Zawadski, Nature 288:373, 1980), prevents a platelet aggregation (Radomski et al., Lancet 2:1057, 1987) and prevents the adhesion and the migration of leukocytes to the vascular wall (Chao et al., J. Immunol., 149:2736, 1992).

The antioxidant properties of the compounds can prevent vascular damages by free radicals, which are caused by activated leukocytes (polymorphonuclear and mononuclear) and vascular cells (e.g., endothelium) and the oxidative modification of LDL, and are the main causes for arteriosclerotic lesion formation and progression (Steinberg et al., N. Engl. J. Med. 320:915, 1989).

Owing to these surprising pharmacological properties, the new compounds of general formula I according to the invention are suitable for preventing and treating the following diseases, especially:

Arteriosclerosis
hypertension
vasospasms (coronary and cerebral)
diabetic vasculopathies (e.g., neuropathy, nephropathy, retinopathy)
cardiac and cerebral ischemia
myocardial infarction
stroke
reperfusion syndrome after ischemia (heart, brain, etc.)
inflammations
rheumatic arthritis
bronchial asthma
nephropathy (e.g., glomerulonephritis)
neurodegenerative diseases (e.g., Alzheimer's disease)

These actions have not been described for the 17-halomethylene-estratrienes and represent completely new and unexpected possibilities in the prevention and treatment of the above-mentioned diseases.

The invention also relates to pharmaceutical preparations that contain compounds of general formula I.

The administration is done depending on the application:

In the case of oral administration, for example, in the form of tablets, soft gelatin capsules, which contain solutions that are used in soft gelatin capsules, aqueous or oily suspensions, emulsions, pills, lozenges, syrups, elixirs or sprays and the like.

In the case of parenteral administration, the compounds of general formula I can be administered in the form of depot injections, implants or muscular, subcutaneous and intravenous injections.

The production of pharmaceutical preparations that contain compounds of general formula I is carried out according to methods known from the prior art (bibliographic reference). Pharmaceutical preparations should contain 17-difluoromethylene-estratrienes at an active ingredient concentration of 0.1–100 mg/kg/day. The respective active ingredient concentration depends on the respective disease to be treated or the severity of the respective disease.

The invention also relates to a process for the production of the compounds of general formula I. They are produced according to the invention by a 17-keto compound of general formula II

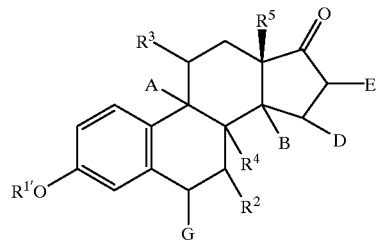

in which
$R^{1'}$ means a hydroxy protective group and
A, B, D, E, G, $R^2$, $R^3$, $R^4$ and $R^5$ can have the meaning indicated in formula I,
being reacted with difluoromethyl-diphenyl-phosphine-oxide or diethyl-(difluoromethyl)-phosphonate in the presence of a strong base in an aprotic solvent at a reflux temperature of 50–100° C., and then optionally the 3-hydroxy protective group being cleaved under the action of an acid and optionally the 3-hydroxy group being etherified.

The 3-hydroxy protective group $R^{1'}$ is either a radical that can easily be cleaved in acid or basic environment, such as, for example, a tetrahydropyranyl (THP) group or a silyl group that is substituted with three identical, two identical or three different straight-chain or branched-chain $C_1$–$C_4$ alkyl and/or aryl radicals, such as, for example, the trimethyl, t-butyldimethyl, methyldiphenyl or t-butyldiphenylsilyl group or a methyl group ($R^1$=$R^{1'}$=$CH_3$), which can be removed, however, only under more drastic conditions.

According to the invention, lithium diisopropylamide, sodium hydride, potassium-t-butylate, butyllithium and the like are suitable as a strong base.

The reaction of the ketone of general formula II is carried out in an aprotic solvent, such as, for example, tetrahydrofuran, dimethyl sulfoxide, dimethylformamide, dioxane or a mixture of these solvents.

The reaction temperature is to lie preferably between 50° C. and 100° C.

The conditions for the cleavage of the 3-hydroxy protective group depend on their nature: protective groups such as the THP group or a silyl radical can be removed under the action of a weak acid such as oxalic acid or an acidic ion exchanger, while the methyl group can be cleaved under the action of strong Lewis acids, e.g., dibutylaluminum hydride.

The etherification of the free 3-hydroxy group is carried out with a reagent that yields radical $R^1$ in a way known in the art.

The production of the 17-ketones that are required for difluoromethylenation with a protected 3-hydroxy function is carried out by reaction of the corresponding, known 3-hydroxy compound with dihydropyran under the effect of para-toluenesulfonic acid in tetrahydrofuran or other methods known to one skilled in the art for the protection of hydroxy groups.

Figure 1:
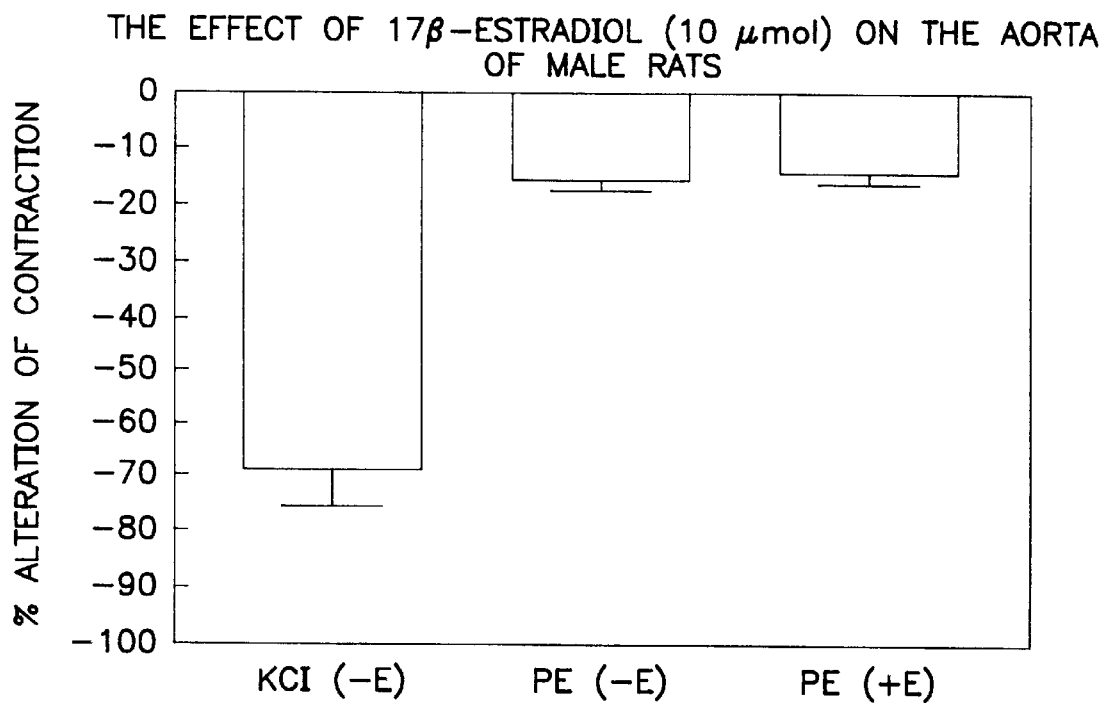
FIG. 1 illustrates the effect of 17β-estradiol on the aorta of male rats
Figure 2:
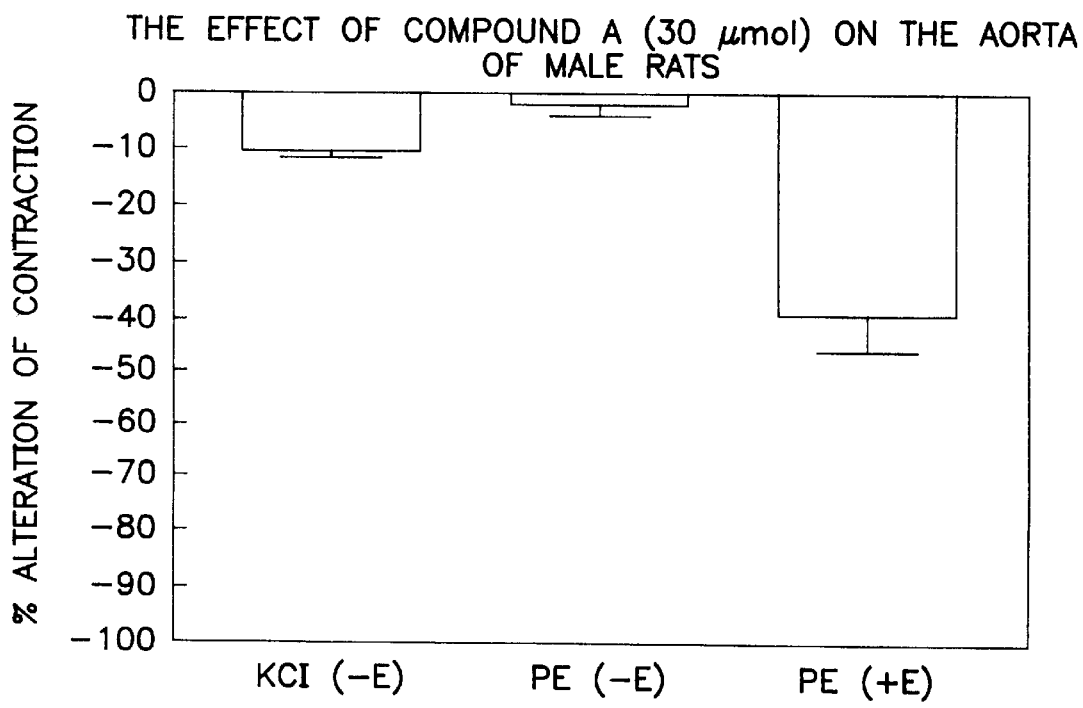
FIG. 2 illustrates the effect of compound A on the aorta of male rats

The following examples are used for a more detailed explanation of this invention:

EXAMPLE 1
17-Difluoromethylene-estra-1,3,5(10)-trien-3-ol 757 mg of difluoromethyl-diphenyl-phosphine-oxide (M. L. Edwards et al. Tetrahedron Letters p. 5571, 1990) in 38 ml of tetrahydrofuran is slowly mixed with 1.5 ml of a 2 M lithium diisopropylamine solution at –50° C., stirred for 1 hour, and mixed with a solution of 1.06 g of 3-tetrahydropyranyloxy-estra-1,3,5 (10)-trien-17-one in 11 ml of tetrahydrofuran. It is stirred for 15 minutes at –50° C., allowed to come to room temperature and stirred for 3.5 hours at a bath temperature of 80° C. For working-up, it is added to water, extracted three times with ethyl acetate, the organic phases are washed neutral with saturated sodium chloride solution, dried on sodium sulfate and evaporated to dryness in a vacuum. 1.3 g of crude 17-difluoromethylene-3-(tetrahydro-pyran-2-yl-oxy)-estra-1,3,5(10)-triene is obtained.

1.3 g of crude 17-difluoromethylene-3-(tetrahydro-pyran-2-yl-oxy)-estra-1,3,5(10)-triene in 30 ml of methanol and 3 ml of water are suspended with 1.3 g of oxalic acid for 1 hour at a bath temperature of 100° C. Then, it is added to water, extracted three times with dichloromethane, washed neutral, dried on sodium sulfate and evaporated to dryness in a vacuum. 1.0 g of crude 17-difluoromethylene-estra-1, 3,5(10)-trien-3-ol, which is chromatographed on silica gel with hexane/ethyl acetate, is obtained. 480 mg of pure 17-difluoromethylene-estra-1,3,5(10)-trien-3-ol is obtained as colorless crystals with a melting point of 154–156° C.

EXAMPLE 2

17-Difluoromethylene-estra-1,3,5(10),6-tetraen-3-ol a) 3-Tetrahydropyranyloxy-estra-1, 3,5(10),6-tetraen-17-one A suspension of 2.6 g of 3-hydroxy-estra-1,3,5(10),6-tetraen-17-one in 26 ml of tetrahydrofuran and 2.6 ml of dihydropyran is stirred with 12.3 mg of para-toluenesulfonic acid for 3 hours at room temperature. Then, it is diluted with ethyl acetate, washed with sodium bicarbonate solution as well as with saturated sodium chloride solution, dried on sodium sulfate and concentrated by evaporation in a vacuum. 3.0 g of 3-tetrahydropyranyloxy-estra-1,3,5(10),6-tetraen-17-one is obtained as colorless crystals.

b) 17-Difluoromethylene-3-tetrahydropyranyloxy-estra-1,3,5(10),6-tetraene

A solution of 715 mg of difluoromethyldiphenylphosphine oxide in 36 ml of tetrahydrofuran is slowly mixed with 1.42 ml of 2 M lithium diisopropylamide solution at a bath temperature of –50° C., and it is stirred for 1 hour. Then, a solution of 1 g of 3-tetrahydropyranyloxy-estra-1,3,5(10),6-tetraen-17-one in 10 ml of tetrahydrofuran is slowly added, stirred for 15 minutes, slowly heated at a bath temperature of from –50° C. to 100° C. and refluxed for 2.5 hours. For working-up, it is added to water, extracted with ethyl acetate, washed with water as well as with saturated sodium chloride solution, dried on sodium sulfate and concentrated by evaporation in a vacuum. 1.1 g of 17-difluoromethylene-3-tetrahydropyranyloxy-estra-1,3,5(10), 6-tetraene is obtained as colorless crystals.

c) 17-Difluoromethylene-estra-1,3,5(10),6-tetraen-3-ol

A suspension of 1.1 g of 17-difluoromethylene-3-tetrahydropyranyloxy-estra-1,3,5(10),6-tetraene in 25 ml of methanol and 2.5 ml of water is refluxed at a bath temperature of 100° C. with 1.1 mg of oxalic acid for 1.5 hours. Then, it is added to water, extracted with dichloromethane, washed with water, sodium bicarbonate solution as well as with saturated sodium chloride solution, dried on sodium sulfate, concentrated by evaporation in a vacuum and chromatographed on silica gel with hexane/ethyl acetate. 0.6 g of 17-difluoromethylene-estra-1,3,5(10),6-tetraen-3-ol is obtained as colorless crystals with a melting point of 132–134° C., $[\alpha]_D^{22}$ =–167.9° (c=0.505% in pyridine).

EXAMPLE 3

17-Difluoromethylene-11β-methoxy-estra-1,3,5(10)-trien-3-ol a) 11β-Methoxy-3-tetrahydropyranyloxy-estra-1,3,5(10)-trien-17-one A suspension of 2.0 g of 11β-methoxy-3-hydroxy-estra-1,3,5(10)-trien-17-one in 20 ml of toluene, 5 ml of tetrahydrofuran and 3.0 ml of dihydropyran is stirred with 20 mg of para-toluenesulfonic acid for 24 hours at room temperature. Then, 0.5 ml of pyridine is added, diluted with ethyl acetate, washed with sodium bicarbonate solution as well as with saturated sodium chloride solution, dried on sodium sulfate, concentrated by evaporation in a vacuum and chromatographed on silica gel with hexane/acetone. 1.9 g of 11β-methoxy-3-tetrahydropyranyloxy-estra-1,3,5(10)-trien-17-one is obtained as crystals with a melting point of 147° C., $[\alpha]_D^{22}$=+147.2° (c=0.5% in pyridine).

b) 17-Difluoromethylene-11β-methoxy-3-tetrahydropyranyloxy-estra-1,3,5 (10)-triene A solution of 3 g of difluoromethyldiphenylphosphine oxide in 80 ml of tetrahydrofuran is slowly mixed with 5.85 ml of 2 M lithium diisopropylamide solution at a bath temperature of –50° C., and it is stirred for 1 hour. Then, a solution of 1.8 g of 11β-methoxy-3-tetrahydropyranyloxy-estra-1,3,5(10)-trien-17-one in 40 ml of tetrahydrofuran is slowly added, stirred for 15 minutes, slowly heated at a bath temperature of from –50° C. to 100° C. and refluxed for 2.5 hours. For working-up, it is diluted with ethyl acetate and water, suctioned off on Celite, rewashed with ethyl acetate, washed with water as well as with saturated sodium chloride solution, dried on sodium sulfate, concentrated by evaporation in a vacuum and chromatographed on silica gel with hexane/ethyl acetate/triethylamine. 1.3 g of 17-difluoromethylene-11β-methoxy-3-tetrahydropyranyloxy-estra-1,3,5(10)-triene is obtained with a melting point of 124–125° C., $[\alpha]_D^{22}$=+60.0° (c=0.505% in pyridine).

c) 17-Difluoromethylene-11β-methoxy-estra-1,3,5(10)-trien-3-ol

A suspension of 1.2 g of 17-difluoromethylene-11β-methoxy-3-tetrahydropyranyloxy-estra-1,3,5(10)-triene in 25 ml of methanol and 2.6 ml of water is refluxed with 1.2 g of oxalic acid for 0.5 hour at a bath temperature of 100° C. Then, it is concentrated by evaporation in a vacuum diluted with ethyl acetate, washed with water, sodium bicarbonate solution as well as with saturated sodium chloride solution, dried on sodium sulfate, concentrated by evaporation in a vacuum and chromatographed on silica gel with hexane/acetone. After crystallization from hexane, 0.9 g of 17-difluoromethylene-11β-methoxy-estra-1,3,5(10)-trien-3-ol is obtained as colorless crystals with a melting point of 245–247° C., $[\alpha]_D^{22}$+77.3° (c=0.535% in pyridine).

EXAMPLE 4

17-Difluoromethylene-estra-1,3,5(10),7-tetraen-3-ol a) 3-Tetrahydropyranyloxy-estra-1,3,5(10),7-tetraen-17-one A suspension of 2.0 g of 3-hydroxy-estra-1,3,5(10), 7-tetraen-17-one in 20 ml of tetrahydrofuran and 2.0 ml of dihydropyran is stirred with 9.6 mg of para-toluenesulfonic acid for 24 hours at room temperature. Then, 0.3 ml of pyridine is added, diluted with ethyl acetate, washed with sodium bicarbonate solution as well as with saturated sodium chloride solution, dried on sodium sulfate, concentrated by evaporation in a vacuum, and chromatographed on silica gel with hexane/acetone. 1.9 g of 3-tetrahydropyranyloxy-estra-1,3,5(10),7-tetraen-17-one is obtained as colorless crystals with a melting point of 147–149° C., $[\alpha]_D^{22}$=+209.7° (c=0.5% in pyridine).

b) 17-Difluoromethylene-3-tetrahydropyranyloxy-estra-1,3,5(10),7-tetraene

A solution of 3 g of difluoromethyldiphenylphosphine oxide in 85 ml of tetrahydrofuran is slowly mixed with 6 ml of 2 M lithium diisopropylamide solution at a bath temperature of –50° C., and it is stirred for 1 hour. Then, a solution of 1.7 g of 3-tetrahydropyranyloxy-estra-1,3,5(10),7-tetraen-17-one in 42 ml of tetrahydrofuran is slowly added, stirred for 15 minutes, slowly heated at a bath temperature of from –50° C. to 100° C. and refluxed for 2.5 hours. For working-up, it is diluted with ethyl acetate and water, suctioned off on Celite, rewashed with ethyl acetate, washed with water as well as with saturated sodium chloride solution, dried on sodium sulfate, concentrated by evaporation in a vacuum and chromatographed on silica gel with hexane/ethyl acetate/triethylamine. 1.0 g of 17-difluoromethylene-3-tetrahydropyranyloxy-estra-1,3,5 (10),7-tetraene is obtained as colorless crystals with a melting point of 83–84° C., $[\alpha]_D^{22}$=+139.6° (c=0.5% in pyridine).

c) 17-Difluoromethylene-estra-1,3,5(10),7-tetraen-3-ol

A suspension of 950 mg of 17-difluoromethylene-3-tetrahydropyranyloxy-estra-1,3,5(10),7-tetraene in 20 ml of methanol and 2.0 ml of water is refluxed with 950 mg of oxalic acid for 0.5 hour at a bath temperature of 100° C. Then, it is concentrated by evaporation in a vacuum diluted with ethyl acetate, washed with water, sodium bicarbonate solution as well as with saturated sodium chloride solution, dried on sodium sulfate, concentrated by evaporation in a vacuum and chromatographed on silica gel with hexane/ethyl acetate. 0.6 g of 17-difluoromethylene-estra-1,3,5(10),7-tetraen-3-ol is obtained as colorless crystals with a melting point of 126–129° C., $[\alpha]_D^{22}$=+163.7° (c=0.505% in pyridine)

EXAMPLE 5

17-Difluoromethylene-estra-1,3,5(10),8-tetraen-3-ol a) 3-Tetrahydropyranyloxy-estra-1,3,5(10),8-tetraen-17-one A suspension of 2.0 g of 3-hydroxy-estra-1,3,5(10),8-tetraen-17-one in 20 ml of tetrahydrofuran and 2.0 ml of dihydropyran is stirred with 9.4 mg of para-toluenesulfonic acid for 3 hours at room temperature. Then, 0.3 ml of pyridine is added, diluted with ethyl acetate, washed with sodium bicarbonate solution as well as with saturated sodium chloride solution, dried on sodium sulfate, concentrated by evaporation in a vacuum and chromatographed on silica gel with hexane/acetone/triethylamine. 2.4 g of 3-tetrahydropyranyloxy-estra-1,3,5(10),8-tetraen-17-one is obtained as colorless crystals with a melting point of 122–125° C., $[\alpha]_D^{22}$=+0.00° (c=0.515% in pyridine).

b) 17-Difluoromethylene-3-tetrahydropyranyloxy-estra-1,3,5(10),8-tetraene

A solution of 2.7 g of difluoromethyldiphenylphosphine oxide in 85 ml of tetrahydrofuran is slowly mixed with 5.3 ml of 2 M lithium diisopropylamide solution at a bath temperature of −50° C., and it is stirred for 1 hour. Then, a solution of 1.5 g of 3-tetrahydropyranyloxy-estra-1,3,5(10),8-tetraen-17-one in 42 ml of tetrahydrofuran is slowly added, stirred for 15 minutes, slowly heated at a bath temperature of from −50° C. to 100° C. and refluxed for 2.5 hours. For working-up, it is diluted with ethyl acetate and water, washed with water, dried on sodium sulfate, concentrated by evaporation in a vacuum and chromatographed on silica gel with hexane/ethyl acetate. 1.0 g of 17-difluoromethylene-3-tetrahydropyranyloxy-estra-1,3,5(10),8-tetraene is obtained as colorless crystals with a melting point of 124–125° C., $[\alpha]_D^{22}$=+2.0° (c =0.525% in pyridine).

c) 17-Difluoromethylene-estra-1, 3,5(10),8-tetraen-3-ol

A suspension of 927 mg of 17-difluoromethylene-3-tetrahydropyranyloxy-estra-1,3,5(10),8-tetraene in 20 ml of methanol and 2.0 ml of water is refluxed with 950 mg of oxalic acid for 0.5 hour at a bath temperature of 100° C. Then, it is concentrated by evaporation in a vacuum diluted with ethyl acetate, washed three times with water, once with sodium bicarbonate solution as well as with saturated sodium chloride solution, dried on sodium sulfate and concentrated by evaporation in a vacuum. After crystallization from hexane, 0.5 g of 17-difluoromethylene-estra-1,3,5 (10),8-tetraen-3-ol is obtained as colorless crystals with a melting point of 127–128° C., $[\alpha]_D^{22}$=−1.5° (c=0.515% in pyridine).

EXAMPLE 6

17-Difluoromethylene-estra-1,3,5(10),9(11)-tetraen-3-ol a) 3-Tetrahydropyranyloxy-estra-1,3,5(10),9(11)-tetraen-17-one A suspension of 2.0 g of 3-hydroxy-estra-1,3,5(10),9(11)-tetraen-17-one in 20 ml of tetrahydrofuran and 3.0 ml of dihydropyran is stirred with 15 mg of para-toluenesulfonic acid for 29 hours at room temperature. Then, 0.3 ml of pyridine is added, diluted with ethyl acetate, washed with sodium bicarbonate solution as well as with saturated sodium chloride solution, dried on sodium sulfate, concentrated by evaporation in a vacuum and chromatographed on silica gel with hexane/acetone/triethylamine. 2.3 g of 3-tetrahydropyranyloxy-estra-1,3,5(10),9(11)-tetraen-17-one is obtained as a colorless oil, $[\alpha]_D^{22}$=+122.5° (c=0.515% in pyridine).

b) 17-Difluoromethylene-3-tetrahydropyranyloxy-estra-1,3,5(10),9(11)-tetraene

A solution of 3.85 g of difluoromethyldiphenylphosphine oxide in 107 ml of tetrahydrofuran is slowly mixed with 7.6 ml of 2 M lithium diisopropylamide solution at a bath temperature of −50° C., and it is stirred for 1 hour. Then, a solution of 2.14 g of 3-tetrahydropyranyloxy-estra-1,3,5(10),9(11)-tetraen-17-one in 42 ml of tetrahydrofuran is slowly added, stirred for 15 minutes, slowly heated at a bath temperature of from −50° C. to 100° C. and refluxed for 2.5 hours. For working-up, it is diluted with ethyl acetate and water, suctioned off on Celite, rewashed with ethyl acetate, washed with water as well as with saturated sodium chloride solution, dried on sodium sulfate, concentrated by evaporation in a vacuum and chromatographed on silica gel with hexane/ethyl acetate/triethylamine. 1.0 g of 17-difluoromethylene-3-tetrahydropyranyloxy-estra-1,3,5(10),9(11)-tetraene is obtained as a colorless oil, $[\alpha]_D^{22}$+ 52.6° (c=0.5% in pyridine).

c) 17-Difluoromethylene-estra-1,3,5(10),9(11)-tetraen-3-ol

A suspension of 900 mg of 17-difluoromethylene-3-tetrahydropyranyloxy-estra-1,3,5(10),9(1l)-tetraene in 19 ml of methanol and 1.9 ml of water is refluxed with 900 mg of oxalic acid for 0.5 hour at a bath temperature of 100° C. Then, it is concentrated by evaporation in a vacuum diluted with ethyl acetate, washed three times with water, once with sodium bicarbonate solution as well as with saturated sodium chloride solution, dried on sodium sulfate, concentrated by evaporation in a vacuum and chromatographed on silica gel with hexane/ethyl acetate. After crystallization from hexane, 0.5 g of 17-difluoromethylene-estra-1,3,5(10),9(11)-tetraen-3-ol is obtained as colorless crystals with a melting point of 134–135° C., $[\alpha]_D^{22}$=+89° (c=0.515% in pyridine).

EXAMPLE 7

17-Difluoromethylene-3-methoxy-estra-1,3,5(10),15-tetraene

A solution of 9.4 g of diethyl-(difluoromethyl)-phosphonate in 150 ml of tetrahydrofuran is slowly mixed with 25 ml of 2 M lithium diisopropylamide solution at a bath temperature of −50° C., and it is stirred for 1 hour. Then, a solution of 5.6 g of 3-methoxy-estra-1,3,5(10),15-tetraen-17-one in 173 ml of tetrahydrofuran is slowly added, stirred for 15 minutes, slowly heated at a bath temperature of from −50° C. to 100° C. and refluxed for 6 hours. For working-up, half the volume is concentrated by evaporation in a vacuum, diluted with ethyl acetate, washed with water as well as with saturated sodium chloride solution, dried on sodium sulfate, concentrated by evaporation in a vacuum and chromatographed on silica gel with hexane/ethyl acetate/triethylamine. 3.0 g of 17-difluoromethylene-3-methoxy-estra-1,3,5(10),15-tetraene is obtained as colorless crystals with a melting point of 122–123° C., $[\alpha]_D^{22}$=−120.9° (c=0.515% in pyridine).

EXAMPLE 8

17-Difluoromethylene-estra-1,3,5(10),15-tetraen-3-ol

A solution of 2.4 g of 17-difluoromethylene-3-methoxy-estra-1,3,5(10),15-tetraene in 49 ml of toluene is refluxed with 49 ml of a 1.6 M diisobutylaluminum hydride solution in toluene for 1 hour at a bath temperature of 140° C. Then, it is cooled to room temperature, slowly added to 200 g of ice, mixed with 400 ml of 2 N sulfuric acid, stirred for 1 hour at room temperature, extracted three times with ethyl acetate, the organic phases are washed with water as well as saturated sodium chloride solution, dried on sodium sulfate, concentrated by evaporation in a vacuum and chromatographed on silica gel with hexane/ethyl acetate. 1.37 g of 17-difluoromethylene-estra-1,3,5(10),15-tetraen-3-ol is obtained as colorless crystals with a melting point of 126–127° C., $[\alpha]_D^{22}$=–120.4° (c=0.505% in pyridine).

EXAMPLE 9

17-Difluoromethylene-7β-methyl-estra-1,3,5(10)-trien-3-ol a) 7β-Methyl-3-tetrahydropyranyloxy-estra-1,3,5(10)-trien-17-one A suspension of 1.2 g of 3-hydroxy-7β-methyl-estra-1,3,5(10)-trien-17-one in 12 ml of toluene and 1.2 ml of dihydropyran is stirred with 5.6 mg of para-toluenesulfonic acid for 2 hours at room temperature. Then, it is diluted with ethyl acetate, washed with sodium bicarbonate solution as well as with saturated sodium chloride solution, dried on sodium sulfate, concentrated by evaporation in a vacuum and chromatographed on silica gel with hexane/acetone. 1.22 g of 7β-methyl-3-tetrahydropyranyloxy-estra-1,3,5(10)-trien-17-one is obtained.

b) 17-Difluoromethylene-7β-methyl-3-tetrahydropyranyloxy-estra-1,3,5(10)-triene

A solution of 2 g of difluoromethyldiphenylphosphine oxide in 55 ml of tetrahydrofuran is slowly mixed with 3.9 ml of 2 M lithium diisopropylamide solution at a bath temperature of –50° C, and it is stirred for 1 hour. Then, a solution of 1.15 g of 7β-methyl-3-tetrahydropyranyloxy-estra-1,3,5(10)-trien-17-one in 20 ml of tetrahydrofuran is slowly added, stirred for 15 minutes, slowly heated at a bath temperature of from –50° C. to 100° C. and refluxed for 2.5 hours. For working-up, it is diluted with ethyl acetate and water, suctioned off on Celite, rewashed with ethyl acetate, washed with water as well as with saturated sodium chloride solution, dried on sodium sulfate, concentrated by evaporation in a vacuum and chromatographed on silica gel with hexane/ethyl acetate/triethylamine. 1.3 g is obtained as colorless crystals with a melting point of 85–86° C., $[\alpha]_D^{22}$=–59–4° (c=0.535% in pyridine).

c) 17-Difluoromethylene-7β-methyl-estra-1,3,5(10)-trien-3-ol

A suspension of 1.2 g of 17-difluoromethylene-7β-methyl-3-tetrahydropyranyloxy-estra-1,3,5(10)-triene in 25 ml of methanol and 2.5 ml of water is refluxed with 1.2 g of oxalic acid for 1 hour at a bath temperature of 100° C. Then, it is concentrated by evaporation in a vacuum diluted with ethyl acetate, washed with water, sodium bicarbonate solution as well as with saturated sodium chloride solution, dried on sodium sulfate, concentrated by evaporation in a vacuum and chromatographed on silica gel with hexane/acetone. After crystallization from hexane, 0.9 g of 17-difluoromethylene-7β-methyl-estra-1,3,5(10)-trien-3-ol is obtained as colorless crystals with a melting point of 119–120° C., $[\alpha]_D^{22}$=–10.6° (c=0.5% in pyridine).

EXAMPLE 10

17-Difluoromethylene-8α-estra-1,3,5(10)-trien-3-ol a) 3-Tetrahydropyranyloxy-8α-estra-1,3,5(10)-trien-17-one A suspension of 2.0 g of 3-hydroxy-8a-estra-1,3,5(10)-trien-17-one in 20 ml of tetrahydrofuran and 2.0 ml of dihydropyran is stirred with 15 mg of para-toluenesulfonic acid for 24 hours at room temperature. Then, 0.3 ml of pyridine is added, diluted with ethyl acetate, washed with sodium bicarbonate solution as well as with saturated sodium chloride solution, dried on sodium sulfate, concentrated by evaporation in a vacuum and chromatographed on silica gel with hexane/acetone. 2.2 g of 3-tetrahydropyranyloxy-8a-estra-1,3,5(10)-trien-17-one is obtained as colorless crystals with a melting point of 153–155° C., $[\alpha]_D^{22}$=+47.5° (c=0.53% in pyridine).

b) 17-Difluoromethylene-3-tetrahydropyranyloxy-8α-estra-1,3,5(10)-triene

A solution of 3.5 g of difluoromethyldiphenylphosphine oxide in 100 ml of tetrahydrofuran is slowly mixed with 7 ml of 2 M lithium diisopropylamide solution at a bath temperature of =50° C., and it is stirred for 1 hour. Then, a solution of 2 g of 3-tetrahydropyranyloxy-8α-estra-1,3,5(10)-trien-17-one in 50 ml of tetrahydrofuran is slowly added, stirred for 15 minutes, slowly heated at a bath temperature of from –50° C. to 100° C. and refluxed for 2 hours. For working-up, it is diluted with ethyl acetate and water, suctioned off on Celite, rewashed with ethyl acetate, washed with water as well as with saturated sodium chloride solution, dried on sodium sulfate, concentrated by evaporation in a vacuum and chromatographed on silica gel with hexane/ethyl acetate/triethylamine. 1.3 g of 17-difluoromethylene-3-tetrahydropyranyloxy-8α-estra-1,3,5(10)-triene is obtained as colorless crystals with a melting point of 90–91° C., $[\alpha]_D^{22}$=–9.2° (c=0.5% in pyridine).

c) 17-Difluoromethylene-8α-estra-1,3,5(10)-trien-3-ol

A suspension of 1.2 g of 17-difluoromethylene-3-tetrahydropyranyloxy-8α-estra-1,3,5(10)-triene in 25 ml of methanol and 2.5 ml of water is refluxed with 1.2 mg of oxalic acid for 0.5 hour at a bath temperature of 100° C. Then, it is concentrated by evaporation in a vacuum diluted with ethyl acetate, washed with water, sodium bicarbonate solution as well as with saturated sodium chloride solution, dried on sodium sulfate, concentrated by evaporation in a vacuum and chromatographed on silica gel with hexane/ethyl acetate. 0.9 g of 17-difluoromethylene-8α-estra-1,3,5(10)-trien-3-ol is obtained as colorless crystals with a melting point of 119–120° C., $[\alpha]_D^{22}$=–10.6° (c=0.5% in pyridine).

EXAMPLE 11

17-Difluoromethylene-3-methoxy-18-methyl-estra-1,3,5(10)-triene

A solution of 9.4 g of diethyl-(difluoromethyl)-phosphonate in 150 ml of tetrahydrofuran is slowly mixed with 25 ml of 2 M lithium diisopropylamide solution at a bath temperature of –50° C., and it is stirred for 1 hour. Then, a solution of 6 g of 3-methoxy-18-methyl-estra-1,3,5(10)-trien-17-one in 173 ml of tetrahydrofuran is slowly added, stirred for 15 minutes, slowly heated at a bath temperature of from –50° C. to 100° C. and refluxed for 6 hours. For working-up, it is diluted with ethyl acetate, washed with water as well as with saturated sodium chloride solution, dried on sodium sulfate, concentrated by evaporation in a vacuum and chromatographed on silica gel with hexane/ethyl acetate. 5.4 g of 17-difluoromethylene-3-methoxy-18-methyl-estra-1,3,5(10)-triene is obtained as colorless crystals with a melting point of 145–146° C., $[\alpha]_D^{22}$=+40.2° (c=0.515% in pyridine).

EXAMPLE 12

17-Difluoromethylene-18-methyl-estra-1,3,5(10)-trien-3-ol

A solution of 5 g of 17-difluoromethylene-3-methoxy-18-methyl-estra-1,3,5(10)-triene in 95 ml of toluene is refluxed with 95 ml of a 1.6 M diisobutylaluminum hydride solution in toluene for 3 hours at a bath temperature of 140° C. Then, it is cooled to room temperature, slowly added to 200 g of ice, mixed with 400 ml of 1 M sulfuric acid, stirred for 1 hour at room temperature, extracted three times with ethyl acetate, the organic phases are washed with water as well as with saturated sodium chloride solution, dried on sodium sulfate, concentrated by evaporation in a vacuum and chromatographed on silica gel with hexane/ethyl acetate. 4.5 g of 17-difluoromethylene-18-methyl-estra-1,3,5(10)-trien-3-ol is obtained as colorless crystals with a melting point of 120–121° C., $[\alpha]_D^{22}$=+37.8° (c=0.5% in pyridine).

What is claimed is:

1. A pharmaceutical preparation comprising an effective amount of a compound of formula I

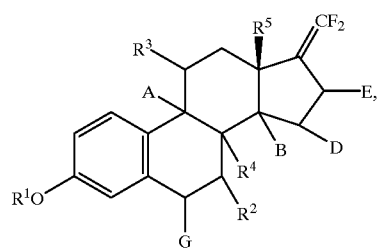

wherein $R^1$ is a hydrogen atom or a $C_1$–$C_{10}$ alkyl group, $R^5$ is a methyl or ethyl group, and $R^2$ is a hydrogen atom or a $C_{1-10}$ alkyl group in α- or β-position, $R^3$ is a hydrogen atom or a $C_1$–$C_{10}$ alkyloxy group in α- or β-position, $R^4$ is a hydrogen atom in α- or β-position, and A, B, D, F and G each are a hydrogen atom, and optionally wherein at least one of substituent pairs G and $R^2$, $R^2$ and $R^4$, $R^4$ and A, A and $^3$, B and D, or D and E mean a double bond, and a pharmaceutically compatible vehicle.

2. A method of treating menopausal symptoms, comprising administering to a patient in need of such treatment an effective amount of a compound of formula I

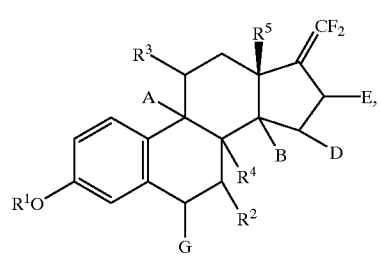

wherein $R^1$ is a hydrogen atom or a $C_1$–$C_{10}$ alkyl group, $R^5$ is a methyl or ethyl group, and $R^2$ is a hydrogen atom or a $C_1$–$C_{10}$ alkyl group in α- or β-position, $R^4$ is a hydrogen atom or a $C_1$–$C_{10}$ alkyloxy group in α- or β-position, $R^4$ is a hydrogen atom in α- or β-position, and A, B, D, E and G each are a hydrogen atom, and optionally wherein at least one of substituent pairs G and $R^2$, $R^2$ and $R^4$, $R^4$ and A, A and $R^3$, B and D, or D and E mean a double bond.

3. A method of treating arteriosclerosis, hypertension, coronary or cerebral vasospasm, diabetic neuropathy, diabetic nephropathy, diabetic retinopathy, cardiac or cerebral ischemia, myocardial infarction, stroke reperfusion syndrome after ischemia, inflammation, rheumatic arthritis, bronchial asthma, glomerulonephritis or Alzheimer's disease, comprising administering to a patient in need of such treatment an effective amount of a compound of formula I

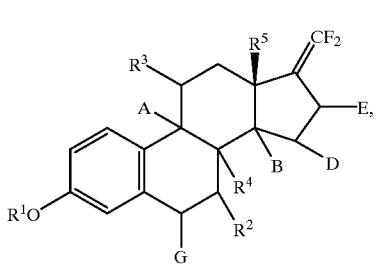

wherein $R^1$ is a hydrogen atom or a $C_1$–$C_{10}$ alkyl group, $R^5$ is a methyl or ethyl group, and $R^2$ is a hydrogen atom or a $C_1$–$C_{10}$ alkyl group in α- or β-position, $R^3$ is a hydrogen atom or a $C_1$–$C_{10}$ alkyloxy group in α- or β-position, $R^4$ is a hydrogen atom in α- or β-position, and A, B, D, E and G each are a hydrogen atom, and optionally wherein at least one of substituent pairs G and $R^2$, $R^2$ and $R^4$, $R^4$ and A, A and $R^3$, B and D, or D and E mean a double bond.

4. A method of ameliorating the symptoms of arteriosclerosis, hypertension, coronary or cerebral vasospasm, diabetic neuropathy, diabetic nephropathy, diabetic retinopathy, cardiac or cerebral ischemia, myocardial infarction, stroke reperfusion syndrome after ischernia, inflammation, rheumatic arthritis, bronchial asthna, glomerulonephritis or Alzheimer's disease, comprising administering to a patient in need of such treatment an effective amount of a compound of formula I

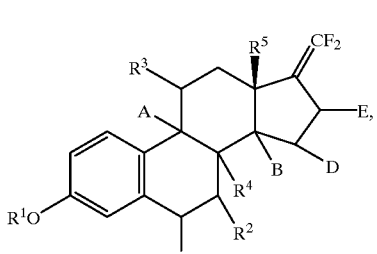

wherein $R^1$ is a hydrogen atom or a $C_1$–$C_{10}$ alkyl group, $R^5$ is a methyl or ethyl group, and $R^2$ is a hydrogen atom or a $C_1$–$C_{10}$ alkyl group in α- or β-position, $R^3$ is a hydrogen atom or a $C_1$–$C_{10}$ alkyloxy group in α- or β-position, $R^4$ is a hydrogen atom in α- or β-position, and A, B, D, E and G each are a hydrogen atom, and optionally wherein at least one of substituent pairs G and $R^2$, $R^2$ and $R^4$, $R^4$ and A, A and $R^3$, B and D, or D and E mean a double bond.

* * * * *